United States Patent
Matheny

(10) Patent No.: US 9,078,882 B2
(45) Date of Patent: Jul. 14, 2015

(54) COMPOSITIONS AND METHODS FOR PREVENTING CARDIAC ARRHYTHMIA

(71) Applicant: CorMatrix Cardiovascular, Inc., Roswell, GA (US)

(72) Inventor: Robert G Matheny, Norcross, GA (US)

(73) Assignee: CORMATRIX CARDIOIOVASCULAR, INC., Roswell, GA (US)

(*) Notice: Subject to any disclaimer, the term of this patent is extended or adjusted under 35 U.S.C. 154(b) by 0 days.

(21) Appl. No.: 14/622,085

(22) Filed: Feb. 13, 2015

(65) Prior Publication Data

US 2015/0164960 A1 Jun. 18, 2015

Related U.S. Application Data

(63) Continuation of application No. 12/707,427, filed on Feb. 17, 2010, now Pat. No. 8,980,296.

(51) Int. Cl.

| | | |
|---|---|---|
| *A61K 35/34* | (2015.01) | |
| *A61K 35/36* | (2015.01) | |
| *A61K 35/12* | (2015.01) | |
| *A61K 35/38* | (2015.01) | |
| *A61K 35/37* | (2015.01) | |
| *A61K 35/407* | (2015.01) | |
| *A61P 9/06* | (2006.01) | |
| *A61P 3/06* | (2006.01) | |
| *A61P 29/00* | (2006.01) | |
| *A61K 35/22* | (2015.01) | |
| *A61K 31/366* | (2006.01) | |
| *A61K 31/40* | (2006.01) | |
| *A61K 31/405* | (2006.01) | |
| *A61K 31/22* | (2006.01) | |
| *A61K 31/505* | (2006.01) | |
| *A61K 31/44* | (2006.01) | |
| *A61K 31/47* | (2006.01) | |
| *A61K 31/138* | (2006.01) | |
| *A61K 31/216* | (2006.01) | |
| *A61K 31/5377* | (2006.01) | |
| *A61K 31/165* | (2006.01) | |

(52) U.S. Cl.
CPC ............. *A61K 35/407* (2013.01); *A61K 31/138* (2013.01); *A61K 31/165* (2013.01); *A61K 31/216* (2013.01); *A61K 31/22* (2013.01); *A61K 31/366* (2013.01); *A61K 31/40* (2013.01); *A61K 31/405* (2013.01); *A61K 31/44* (2013.01); *A61K 31/47* (2013.01); *A61K 31/505* (2013.01); *A61K 31/5377* (2013.01); *A61K 35/22* (2013.01); *A61K 35/38* (2013.01)

(58) Field of Classification Search
CPC ....... A61K 35/34; A61K 35/12; A61K 35/36; A61K 35/545; A61K 38/18; A61K 38/1833; A61K 38/193; A61K 38/30; A61K 38/39; A61K 48/00; A61L 27/3633; A61L 2300/236; A61L 2300/41; A61L 2300/422

See application file for complete search history.

(56) References Cited

U.S. PATENT DOCUMENTS

2006/0134079 A1\* 6/2006 Sih et al. .................... 424/93.21

\* cited by examiner

*Primary Examiner* — Audrea Buckley
(74) *Attorney, Agent, or Firm* — Francis Law Group

(57) ABSTRACT

Disclosed herein are compositions and methods for treating or preventing cardiac arrhythmia in a subject.

3 Claims, No Drawings

COMPOSITIONS AND METHODS FOR PREVENTING CARDIAC ARRHYTHMIA

CROSS-REFERENCE TO RELATED PATENT APPLICATIONS

This application is a division of U.S. application Ser. No. 12/707,427, filed on Feb. 17, 2010, which claims the benefit of U.S. Provisional Application No. 61/153,402, filed on Feb. 18, 2009.

BACKGROUND OF THE INVENTION

Cardiac arrhythmias present a significant health problem. Cardiac arrhythmias include but are not limited to ventricular tachycardias, supraventricular tachycardias, and atrial fibrillation. Of these, atrial fibrillation is the most common cardiac arrhythmia.

It has been estimated that over one million people in the United States alone suffer from atrial fibrillation. The incidence of atrial fibrillation is expected to increase over the next several decades as populations in the United States and Europe trend older because atrial fibrillation tends to become more common with increasing age.

Arrhythmias after cardiac surgery are a major cause of morbidity and mortality. Tolerability of arrhythmia is less in the postoperative period than for similar arrhythmias in the preoperative period. Hemodynamic instability is more likely due to the possibility of myocardial dysfunction. Cardiopulmonary bypass, injury to the conduction system during surgery, metabolic and electrolyte abnormalities, especially hypokalemia and hypomagnesemia, contribute to the increased incidence of postoperative arrhythmias. Stress of the surgery with enhanced sympathetic tone and use of inotropic support are added factors. Delayed arrhythmia can occur due to scar-related re-entry.

Atrial fibrillation can be treated with medication intended to maintain normal sinus rhythm and/or decrease ventricular response rates. Specifically, many of the past attempts have been confined to pharmacotherapy, radiofrequency ablation, use of implantable devices, and related approaches. While drug therapy remains a popular route for reducing some arrhythmic events, there has been recognition that systemic effects are often poorly tolerated. Moreover, there is belief that proarrhythmic tendencies exhibited by many drugs can increase mortality in many situations. It would be desirable to have more effective methods for treating or preventing cardiac arrhythmias.

BRIEF SUMMARY OF THE INVENTION

In accordance with the purpose of this invention, as embodied and broadly described herein, this invention relates to compositions and methods for treating or preventing cardiac arrhythmia in a subject. Additional advantages of the disclosed methods and compositions will be set forth in part in the description which follows, and in part will be understood from the description, or may be learned by practice of the disclosed methods and compositions.

The advantages of the disclosed methods and compositions will be realized and attained by means of the elements and combinations particularly pointed out in the appended claims. It is to be understood that both the foregoing general description and the following detailed description are exemplary and explanatory only and are not restrictive of the invention as claimed.

DETAILED DESCRIPTION OF THE INVENTION

The disclosed methods and compositions may be understood more readily by reference to the following detailed description of particular embodiments and the Example included therein and to the following description.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a peptide is disclosed and discussed and a number of modifications that can be made to a number of molecules including the peptide are discussed, each and every combination and permutation of peptide and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed, it is understood that each of these additional steps can be performed with any specific embodiment or combination of embodiments of the disclosed methods, and that each such combination is specifically contemplated and should be considered disclosed.

Those skilled in the art will recognize, or be able to ascertain using no more than routine experimentation, many equivalents to the specific embodiments of the method and compositions described herein. Such equivalents are intended to be encompassed by the following claims.

It is understood that the disclosed methods and compositions are not limited to the particular methodology, protocols, and reagents described, as these may vary. It is also to be understood that the terminology used herein is for the purpose of describing particular embodiments only and is not intended to limit the scope of the present invention which will be limited only by the appended claims.

A. DEFINITIONS

Unless defined otherwise, all technical and scientific terms used herein have the same meanings as commonly understood by one of skill in the art to which the disclosed methods and compositions belong. Although any methods and materials similar or equivalent to those described herein can be used in the practice or testing of the present methods and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinence of the cited documents.

It must be noted that as used herein and in the appended claims, the singular forms "a," "an," and "the" include plural referents unless the context clearly dictates otherwise. Thus, for example, reference to "a compound" includes a plurality of such compounds, reference to "the compound" is a reference to one or more compounds and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed. It is also understood that the throughout the application, data are provided in a number of different formats, and that these data represent endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units is also disclosed. For example, if 10 and 15 are disclosed, then 11, 12, 13, and 14 are also disclosed.

Throughout the description and claims of this specification, the word "comprise" and variations of the word, such as "comprising" and "comprises," means "including but not limited to" and is not intended to exclude, for example, other additives, components, integers or steps.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. METHODS

Disclosed herein are methods of treating or preventing a cardiac arrhythmia in a subject. The methods can comprise administering to the cardiac tissue of the subject a therapeutically effective amount of a composition comprising a mammalian extracellular matrix (ECM).

In some aspects, the mammalian ECM is derived from a native source. In some aspects, the mammalian ECM is produced in vitro using mammalian cells. In some aspects, the mammalian ECM is extracted directly from mammalian tissue/organs. In some aspects the composition comprising mammalian ECM further comprises synthetic ECM.

In some aspects, the composition comprising a mammalian ECM inhibits scar formation. In some aspects, the composition comprising a mammalian ECM promotes regeneration of damaged tissue. In some aspects, the composition comprising a mammalian ECM inhibits inflammation.

By "treatment" is meant the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

By "prevent" or "preventing" is meant reducing the frequency or severity of a disease or condition. The term does not require an absolute preclusion of the disease or condition. Rather, this term includes decreasing the chance for disease occurrence. Thus, disclosed are methods of reducing the occurrence and/or severity of a cardiac arrhythmia in a subject, comprising administering to cardiac tissue of the subject a therapeutically effective amount of a composition comprising a mammalian ECM.

The term "therapeutically effective" means that the amount of the composition used is of sufficient quantity to ameliorate one or more causes, symptoms, or sequelae of a disease or disorder. Such amelioration only requires a reduction or alteration, not necessarily elimination, of the cause, symptom, or sequelae of a disease or disorder.

As used herein, the term "cardiac tissue" includes the myocardium, epicardium, endocardium, and pericardium of the heart. The term as used herein also refers to the great vessels leading to or from the heart. The term as used herein also refers to portions of the vagus nerve that innervate the heart.

Thus, in some aspects, the methods comprise administering a composition comprising a mammalian ECM to the heart of the subject. In some aspects, the methods comprise administering a composition comprising a mammalian ECM to the myocardium of the subject. The myocardium can be ventricular myocardium. The myocardium can be atrial myocardium. In some aspects, the methods comprise administering a composition comprising a mammalian ECM to the epicardium of the subject. In some aspects, the methods comprise administering a composition comprising a mammalian ECM to the endocardium of the subject. In some aspects, the methods comprise administering a composition comprising a mammalian ECM to the pericardium of the subject.

In some aspects, the methods comprise administering a composition comprising a mammalian ECM to a great vessel of the subject. In some aspects, the vessel is the superior vena cava, inferior vena cava, pulmonary vein, pulmonary artery, or aorta of the subject. For example, the method can comprise administering a composition comprising a mammalian ECM to the adventitia (external portion) of one or more of the great vessels. In some aspects, the method comprises administering a composition comprising a mammalian ECM to the cardiac circulation. Thus, the method comprises administering a composition comprising a mammalian ECM into a blood vessel or heart chamber.

Parasympathetic innervation of the heart is mediated by the vagus nerve. The right vagus innervates the sinoatrial (SA) node. Parasympathetic hyperstimulation predisposes those affected to bradyarrhythmias. The left vagus when hyperstimulated predisposes the heart to atrioventricular (AV) blocks. Thus, in some aspects, the methods comprise administering a composition comprising a mammalian ECM to a portion of the vagus nerve of the subject that innervates the heart.

As used herein, the term "subject" means any individual who is the target of administration. The subject can be a vertebrate, for example, a mammal. Thus, the subject can be a human. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects. As used herein, the terms "patient" and "subject" can be used interchangeably.

In some aspects, the subject of the disclosed method has been identified as being at risk of developing a cardiac arrhythmia. In some aspects, the subject of the disclosed method has undergone heart surgery, including, but not limited to, open-heart surgery. In some aspects, the subject of the disclosed method has undergone multiple combined heart procedures, including, but not limited to, open heart procedures. In some aspects, the subject of the disclosed method has undergone heart valve surgery. In some aspects, the subject of the disclosed method is at least 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, or 85 years of age. In some aspects, the composition is administered to a subject who has had a myocardial infarction. In some aspects, the subject of the disclosed method has emphysema or chronic obstructive pulmonary disease. In some aspects, the subject of the disclosed method has a history of arrhythmia.

In some aspects, the disclosed method does not comprise administering a patch comprising small intestinal submucosa (SIS) to an opening in the pericardial sac of the heart. In some aspects, the disclosed method does not consist of administering a patch comprising small intestinal submucosa (SIS) to an opening in the pericardial sac of the heart. In some aspects, the mammalian ECM is not SIS. Thus, in some aspects, the composition comprising mammalian ECM does not consist of SIS. In some aspects, the composition comprising mammalian ECM is not a patch. In some aspects, the disclosed method does not comprise administering the composition comprising mammalian ECM as a patch to an opening in the pericardial sac of the heart. In some aspects, the cardiac tissue of the disclosed method is not pericardium. In some aspects, the disclosed method does not comprise administering the composition to the pericardium.

In other aspects, however, the disclosed method comprises administering a patch comprising small intestinal submucosa (SIS) to an opening in the pericardial sac of the heart. The compositions used in the disclosed methods can comprise an additional agent, such as anti-arrhythmia drugs, or non-native cells. In other aspects, the disclosed method comprises administering a patch comprising small intestinal submucosa (SIS) to an opening in the pericardial sac of the heart, but the method further comprises additional steps.

Also disclosed herein is a method of treating or preventing a cardiac arrhythmia in a subject, comprising administering to cardiac tissue of the subject a therapeutically effective amount of a composition comprising a mammalian extracellular matrix and further comprising an anti-arrhythmic drug, a lipid-lowering drug, cells, a protein, or a combination thereof.

1. Cardiac Arrhythmia

Cardiac arrhythmia (also referred to as dysrhythmia) is a term for any of a large and heterogeneous group of conditions in which there is abnormal electrical activity in the heart. The heart beat (pulse) can be too fast or too slow and can be regular or irregular.

Some arrhythmias are life-threatening medical emergencies that can result in cardiac west and sudden death. Others cause symptoms such as an abnormal awareness of heart beat (palpitations) and can be merely annoying. Others may not be associated with any symptoms at all but pre-dispose toward potentially life threatening stroke or embolus.

The term sinus arrhythmia refers to a normal phenomenon of mild acceleration and slowing of the heart rate that occurs with breathing in and out. It is usually quite pronounced in children, and steadily lessens with age. This can also present during meditation breathing exercises that involve deep inhaling and breath holding patterns.

Each heart beat originates as an electrical impulse from a small area of tissue in the right atrium of the heart called the sinus node or sinoatrial (SA) node. The impulse initially causes both of the atria to contract, then activates the atrioventricular (or AV) node which is normally the only electrical connection between the atria and the ventricles or main pumping chambers. The impulse then spreads through both ventricles via the His Purkinje fibers causing a synchronized contraction of the heart muscle.

A heart rate less than 60 beats per minute is a bradycardia. This can be caused by a slowed signal from the sinus node (termed sinus bradycardia), a pause in the normal activity of the sinus node (termed sinus arrest), or by blocking of the electrical impulse on its way from the atria to the ventricles (termed AV block or heart block). Heart block comes in varying degrees and severity. It can be caused by reversible poisoning of the AV node (with drugs that impair conduction) or by irreversible damage to the node.

A heart rate faster than 100 beats per minute is a tachycardia. Tachycardia can result in palpitation; however, tachycardia is not necessarily an arrhythmia. Increased heart rate is a normal response to physical exercise or emotional stress. This is mediated by the sympathetic nervous system's effect on the sinus node, and is called sinus tachycardia. Other things that increase sympathetic nervous system activity in the heart include ingested or injected substances such as caffeine or amphetamines, and an overactive thyroid gland (hyperthyroidism). Heart rate can be increased with sympathomimetic drugs.

Tachycardia that is not sinus tachycardia usually results from the addition of abnormal impulses that can begin by one of three mechanisms: automaticity, re-entry or triggered activity.

Automaticity refers to a cardiac muscle cell firing off an impulse on its own. All of the cells in the heart have the ability to initiate an action potential; however, only some of these cells are designed to routinely trigger heart beats. These cells are found in the conduction system of the heart and include the SA node, AV node, Bundle of HIS and Purkinje fibers. The SA node is a single specialized location in the atrium which has a higher automaticity (a faster pacemaker) than the rest of the heart and therefore is usually responsible for setting the heart rate and initiating each heart beat. Any part of the heart that initiates an impulse without waiting for the SA node is called an ectopic focus and is by definition a pathological phenomenon. This can cause a single premature beat now and then, or, if the ectopic focus fires more often than the SA node, it can produce a sustained abnormal rhythm. Conditions that increase automaticity include sympathetic nervous system stimulation and hypoxia. The resulting heart rhythm depends on where the first signal begins. If it is the SA node, the rhythm remains normal but rapid; if it is an ectopic focus, many types of arrhythmia can result.

Re-entry arrhythmias occur when an electrical impulse recurrently travels in a tight circle within the heart, rather than moving from one end of the heart to the other and then stopping. Every cardiac cell is able to transmit impulses in every direction but can only do so once within a short period of time. Normally, the action potential impulse will spread through the heart quickly enough that each cell will only respond once. However, if conduction is abnormally slow in some areas, part of the impulse will arrive late and potentially be treated as a new impulse. Depending on the timing, this can produce a sustained abnormal circuit rhythm. Re-entry circuits are responsible for atrial flutter, most paroxysmal supraventricular tachycardias, and dangerous ventricular tachycardia. When an entire chamber of the heart is involved in multiple micro-reentry circuits and therefore quivering with chaotic electrical impulses, it is said to be in fibrillation.

Fibrillation can affect the atrium (atrial fibrillation) or the ventricle (ventricular fibrillation). If left untreated, ventricular fibrillation (VF, or V-fib) can lead to death within minutes.

Triggered beats occur when problems at the level of the ion channels in individual heart cells result in abnormal propagation of electrical activity and can lead to sustained abnormal rhythm. Triggered beats are relatively rare but can result from the action of anti-arrhythmic drugs.

Arrhythmia can be classified by rate (normal, tachycardia, bradycardia), or mechanism (automaticity, re-entry, fibrillation).

It is also appropriate to classify arrhythmia by site of origin. For example, atrial arrhythmias include premature atrial contractions (PACs), wandering atrial pacemaker, multifocal atrial tachycardia, atrial flutter, and atrial fibrillation (Afib). Junctional arrhythmias include supraventricular tachycardia (SVT), AV nodal reentrant tachycardia (the most common cause of paroxysmal supra-ventricular tachycardia (PSVT)), junctional rhythm, junctional tachycardia, and premature junctional complex. Atrioventricular arrhythmias include AV reentrant tachycardia (occurs when a re-entry circuit crosses between the atria and ventricles somewhere other than the AV node).

Ventricular Arrhythmias include Premature Ventricular Contractions (PVC) (sometimes called Ventricular Extra Beats (VEBs)), Accelerated idioventricular rhythm, Monomorphic Ventricular tachycardia, Polymorphic ventricular tachycardia, and Ventricular fibrillation.

Heart blocks (also known as AV blocks, the most common causes of bradycardia) include First degree heart block (PR interval greater than 200 ms in length on the surface ECG), Second degree heart block (Type 1 and 2), and Third degree heart block (also known as complete heart block).

Cardiac arrhythmias are often first detected by auscultation of the heartbeat with a stethoscope or by feeling peripheral pulses. These methods cannot usually diagnose specific arrhythmias but can give a general indication of the heart rate and whether it is regular or irregular. Not all of the electrical impulses of the heart produce audible or palpable beats; in many cardiac arrhythmias, the premature or abnormal beats do not produce an effective pumping action and are experienced as "skipped" beats.

The simplest specific diagnostic test for assessment of heart rhythm is the electrocardiogram (abbreviated ECG or EKG). A Holter monitor is an EKG recorded over a 24-hour period, to detect arrhythmias that can happen briefly and unpredictably throughout the day.

Sudden arrhythmia death syndrome (SADS) is a term used to describe sudden death due to cardiac arrest brought on by an arrhythmia. Often, the subject has no symptoms before dying suddenly. The most common cause of sudden death in the United States is coronary artery disease. Approximately 300,000 people die suddenly of this cause every year in the United States. SADS can also be caused by, for example, many inherited conditions and heart diseases that can affect young people.

In children, for example, viral myocarditis, long Q-T syndrome, Brugada syndrome, Catecholaminergic polymorphic ventricular tachycardia and hypertrophic cardiomyopathy, and arrhythmogenic right ventricular dysplasia can cause SADS.

In some aspects, the cardiac arrhythmia is atrial fibrillation or ventricular fibrillation.

2. Administration

In some aspects, the mammalian ECM is a patch in a form such as a sheet, plug, a laminate, a weave, a polymer matrix, a plurality of strands, or one or more strips. Thus, in some aspects, the mammalian ECM is placed into direct contact with the cardiac tissue of a subject during heart surgery. In some aspects, the composition comprising a mammalian ECM is administered to an opening in the pericardial sac of the heart. In some aspects, the composition overlaps the opening in the pericardial sac. Thus, the composition comprising a mammalian ECM can be administered to the surgical opening of the pericardium during or after heart surgery. In another aspect, the mammalian ECM can be placed into contact with cardiac structures, such as the great vessels, e.g., aorta, pulmonary artery, pulmonary vein, superior vena cava, and inferior vena cava.

Wherein the mammalian ECM is in a solid form such as a sheet, a plug, a laminate, a weave, a polymer matrix, a plurality of strands, or one or more strips, the composition can be attached to the cardiac tissue using standard means available in the art. For example, the composition comprising mammalian ECM can be attached to the cardiac tissue with sutures, bioadhesives such as fibrin glue, staples, and the like.

The disclosed compounds and compositions comprising a mammalian ECM can be administered in any suitable manner. For example, the compositions can be administered parenterally (e.g., intramuscular injection), topically or the like. Thus, in some aspects, the composition comprising a mammalian ECM is injectable. The disclosed compositions can be injected into the cardiac tissue using ordinary means. For example, the composition comprising a mammalian ECM can be delivered to the cardiac tissue via a syringe or a cardiac or coronary catheter. Cardiac catheterization (heart cath) is the insertion of a catheter into a chamber or vessel of the heart. This can be done for both diagnostic and/or interventional purposes. Coronary catheterization is a subset of this technique, involving the catheterization of the coronary arteries.

Thus, in some aspects, the composition comprising a mammalian ECM can be injected into the myocardium of the heart. In some aspects, the composition comprising a mammalian ECM can be injected into the epicardium of the heart. In some aspects, the composition comprising a mammalian ECM can be injected into the endocardium of the heart. In some aspects, the composition comprising a mammalian ECM can be injected into the pericardium of the heart. In some aspects, the composition comprising a mammalian ECM can be injected between layers of the heart, e.g., between the pericardium and epicardium, between the epicardium and myocardium, and between the myocardium and endocardium.

In some aspects, the composition comprising a mammalian ECM can be administered to the atrial or ventricular septum of the subject. For example, in some aspects, the composition comprising a mammalian ECM can be administered to a ventricular septal defect. A ventricular septal defect (VSD) is a defect in the ventricular septum, the wall dividing the left and right ventricles of the heart. The ventricular septum consists of an inferior muscular and superior membranous portion and is extensively innervated with conducting cardiomyocytes. The membranous portion, which is close to the atrioventricular node, is most commonly affected in adults and older children. Congenital VSDs are collectively the most common congenital heart defects.

In some aspects, the composition comprising a mammalian ECM can be administered to an atrial septal defect (ASD). ASD is a form of congenital heart defect that enables blood flow between the left and right atria via the interatrial septum. The interatrial septum is the tissue that divides the right and left atria. Without this septum, or if there is a defect in this septum, it is possible for blood to travel from the left side of the heart to the right side of the heart, or vice versa. [1] Irrespective of interatrial communication bi-directions, this results in the mixing of arterial and venous blood. The mixing of arterial and venous blood may or may not be hemodynamically significant, if even clinically significant. This mixture of blood may or may not result in what is known as a "shunt". The amount of shunting present, if any, dictates hemodynamic significance (see Pathophysiology below). A "right-to-left-shunt" typically poses the more dangerous scenario (see Pathophysiology below).

The mammalian ECM can be in an aerosol form. Thus, in some aspects, the mammalian ECM can be sprayed on the cardiac tissue of the subject.

The mammalian ECM can be in a particulate form. Particulate mammalian ECM can be administered by injecting an emulsified composition, spraying, layering, packing, dusting, painting, or other similar types of application of the dry particulate, the liquid composition, or the semi-solid compositions.

In some aspects, the composition is administered to the epicardial surface of the heart. Thus, in some aspects, the composition is injected, sprayed, or attached to the epicardial surface of the heart.

The exact amount of the compositions required can vary from subject to subject, depending on the species, age, weight and general condition of the subject, the severity of the disorder being treated. Thus, it is not possible to specify an exact amount for every composition. However, an appropriate amount can be determined by one of ordinary skill in the art using only routine experimentation given the teachings herein. Thus, effective dosages and schedules for administering the compositions can be determined empirically, and making such determinations is within the skill in the art. The dosage ranges for the administration of the compositions are those large enough to produce the desired effect in which the symptom or disorder is affected. The dosage should not be so large as to cause adverse side effects, such as unwanted cross-reactions, anaphylactic reactions, and the like. Generally, the dosage can vary with the age, condition, sex and extent of the disease in the patient, route of administration, or whether other drugs are included in the regimen, and can be determined by one of skill in the art. Dosage can vary and can be administered in one or more dose administrations daily, for one or several days. Guidance can be found in the literature for appropriate dosages for given classes of pharmaceutical products.

Following administration of a disclosed composition for treating, inhibiting, or preventing a cardiac arrhythmia, the efficacy of the method can be assessed in various ways well known to the skilled practitioner. For example, one of ordinary skill in the art will understand that a composition disclosed herein is efficacious in treating a cardiac arrhythmia in a subject using an electrocardiogram.

The compositions disclosed herein can be administered prophylactically to subjects who are at risk for cardiac arrhythmia. The disclosed compositions and methods can also be used, for example, as tools to isolate and test new drug candidates for treating or preventing cardiac arrhythmia. The disclosed compositions can also be used in a variety of ways as research tools. Other uses are disclosed, apparent from the disclosure, and/or will be understood by those in the art.

3. Combination Therapy

The herein disclosed methods can further comprise treating the subject with conventional antiarrhythmia therapies. For example, there are many classes of antiarrhythmic medications with different mechanisms of action and many different individual drugs within these classes. Thus, the method can further comprise administering to the subject one or more antiarrhythmic medications.

Some arrhythmias, e.g., atrial fibrillation, cause blood clotting within the heart and increase risk of embolus and stroke. Anticoagulant medications such as warfarin and heparin, and anti-platelet drugs such as aspirin can reduce the risk of clotting. Thus, the method can further comprise administering to the subject an anticoagulant.

Arrhythmias can also be treated electrically, by applying a shock across the heart—either externally to the chest wall, or internally to the heart via implanted electrodes or intra-operatively. Cardioversion can be achieved either pharmacologically or via the application of a shock synchronized to the underlying heartbeat. It is used for treatment of supraventricular tachycardias. In elective cardioversion, the recipient is usually sedated or lightly anesthetized for the procedure. For example, atrial flutter can be treated by cardioversion. Thus, the method can further comprise treating the subject with cardioversion.

With synchronized cardioversion, a reversion shock is delivered by way of pads or paddles of a selected amount of electric current over a predefined number of milliseconds at the optimal moment in the cardiac cycle which corresponds to the R wave of the QRS complex on the ECG. Timing the shock to the R wave prevents the delivery of the shock during the vulnerable period (or relative refractory period) of the cardiac cycle, which could induce ventricular fibrillation.

Defibrillation differs from cardioversion in that the shock is not synchronized to a cardiac cycle. It is needed for the chaotic rhythm of ventricular fibrillation and is also used for pulseless ventricular tachycardia. Often, more electricity is required for defibrillation than for cardioversion. Because most subjects with ventricular fibrillation are unconscious, there is generally no need for sedation. Thus, the method can further comprise treating the subject with defibrillation.

Defibrillation or cardioversion can be accomplished by an implantable cardioverter-defibrillator (ICD). Thus, the method can further comprise administering to the subject an ICD.

Electrical treatment of arrhythmia also includes cardiac pacing. Temporary pacing can be necessary for reversible causes of very slow heartbeats, or bradycardia, (for example, from drug overdose or myocardial infarction). A permanent pacemaker can be placed in situations where the bradycardia is not expected to recover. Thus, the method can further comprise administering to the subject a pacemaker.

Fine probes can in some aspects be inserted through the blood vessels to map electrical activity from within the heart. This allows abnormal areas of conduction to be located very accurately, and subsequently destroyed with heat, cold, electrical or laser probes.

C. COMPOSITIONS

A patch of mammalian ECM has been shown to act as a mechanical scaffold while the body recruits the necessary cells to remodel and repair the cardiac tissue. Disclosed herein is the surprising ability of mammalian ECM to additionally treat and/or prevent cardiac arrhythmia. Thus, disclosed herein are compositions comprising mammalian ECM for use in the disclosed method(s) for treating or preventing cardiac arrhythmia in a subject. The disclosed compositions can be natural or synthetic. The compositions can be de-cellularized or comprise cells such as stem cells.

The herein disclosed compositions comprising mammalian ECM can be in the form of, for example, a patch, an emulsion, an injectable solution, a gel, a fluid, a paste, a powder, a strand, a strip, a spray, a vapor, an aerosol, a cream, or a coating. The composition can further comprise one or more additional components, including, for example, a cell, peptide, polypeptide, protein or other biological moieties. Where the composition is a patch, it can be in a form selected from a sheet, a laminate, a weave, a polymer matrix, a plurality of strands, one or more strips, or a combination thereof.

The herein disclosed compositions comprising mammalian ECM can be made into a particulate and fluidized as described in U.S. Pat. No. 5,275,826 to Badylak, U.S. Pat. No. 6,579,538 to Spievack, and U.S. Pat. No. 6,933,326 to Griffey. Fluidized or emulsified compositions (the liquid or semi-solid forms) can be present at a certain concentration, for example at a concentration of extracellular matrix greater than about 0.001 mg/ml. The concentration of these liquid or semi-solid components of the extracellular matrix composition can be in a range from about 0.001 mg/ml to about 200 mg/ml. The concentrations can further be found in more specific ranges such as for example the following set of ranges: about 5 mg/ml to about 150 mg/ml, about 10 mg/ml to about 125 mg/ml, about 25 mg/ml to about 100 mg/ml, about 20 mg/ml to about 75 mg/ml, about 25 mg/ml to about 60 mg/ml, about 30 mg/ml to about 50 mg/ml, and about 35 mg/ml to about 45 mg/ml, and about 40 mg/ml. to about 42 mg/ml. This set of ranges is exemplary and not intended to be exhaustive. It is contemplated that any value within any of these specifically listed ranges is a reasonable and useful value for a concentration of a liquid, emulsion, gel, paste or other liquid or semi-solid component of the composition.

1. Mammalian Extracellular Matrix

Extracellular matrix materials act as a natural scaffold for repairing soft tissues in the body. Animal studies have shown that the original extracellular matrix material remodels and is replaced by host tissue. Mammalian ECM is a resorbable biomaterial which has been used successfully as a xenogenic tissue graft that induces constructive remodeling of a variety of animal tissues including blood vessels, urinary bladder, dura, abdominal wall, tendons and ligaments. Examples of mammalian ECM include small intestine submucosa (SIS), urinary bladder submucosa (UBS), stomach submucosa (SS), and liver submucosa (LS) or liver basement membrane (LBM).

The remodeling process includes rapid neovascularization and abundant accumulation of mesenchymal and epithelial cells that support extensive deposition of a new extracellular matrix. The noncollagenous portion of for example, the SIS extracellular matrix is composed of various glycoproteins, such as hyaluronic acid, heparin, dermatan and chondroitin sulfate A, as well as FGF-2 and TGF-$\beta$ growth factors.

After processing, mammalian ECM can retain many of the endogenous proteins which act as growth and differentiation factors. These factors stimulate the local environment to populate the mammalian ECM with cells that are then able to differentiate into the original tissue that the mammalian ECM is replacing.

Mammalian ECM is a scaffold matrix of polymerized "structural" proteins that fit into three groups: collagens, glycoproteins, and proteoglycans (which have glycosaminoglycan repeats throughout). These molecules actually polymerize to form the scaffold or matrix of proteins that exists in dynamic interaction with cells and closely placed functional proteins (either on the cells, or bound to a structural protein). Thus, mammalian ECM also includes within its matrix scaffold "functional" proteins that interact with the structural proteins and with migrating or recruited cells, such as stem cells. The matrix functional proteins also interact with protein-expressing cells during the life and maintenance of the matrix scaffold itself as it rebuilds and maintains its components. Some proteins can be both a structural and functional protein, depending on the protein's configuration and placement in the whole matrix.

The ECM of, for example, cardiac tissue is made up of collagen types I (predominant), III, IV, V, and VI, combined which are 92% of the dry weight of the matrix. The ECM of cardiac tissue is also made up of glycosaminoglycans (GAGs), which include chondroitin sulfate A and B, heparan, heparin, and hyaluronic acid. Glycoproteins such as fibronectin and entactin, proteoglycans such as decorin and perlecan, and growth factors such as transforming growth factor beta (TGF-$\beta$), fibroblast growth factor-2 (FGF-2) and vascular endothelial growth factor (VEGF), are key players in the activity of a myocardium regenerating matrix. Furthermore, the precise chemical constitution of the matrix appears to play a role in its function, including, for example, what collagen type is prevalent in the matrix. Thus, the outcome of any tissue regenerative processes can be determined by the structural and functional components of the matrix scaffold that form the basis of the regenerative process.

Facilitating cell adhesion functions in ECM are cell adhesion molecules (CAMs). The CAMs can either be available endogenously or added as an additional component of the composition. CAMs are glycoproteins lodged in the surface of the cell membrane or transmembrane connected to cytoskeletal components of the cell. Specific CAMs include cadherins that are calcium dependent, and more than 30 types are known. Also working as CAMs are integrins which are proteins that link the cytoskeleton of the cell in which they are lodged to the extracellular matrix or to other cells through alpha and beta transmembrane subunits on the integrin protein. Cell migration, embryogenesis, hemostasis, and wound healing are facilitated by the integrins in the matrix. Syndecans are proteoglycans that combine with ligands for initiating cell motility and differentiation. Immunoglobulins provide any necessary immune and inflammatory responses. Selectins promote cell-cell interactions.

i. Native Sources and Preparations

In some aspects, the mammalian ECM is derived from native source. Native extracellular matrix scaffolds and the proteins that form them can be found in their natural environment, i.e., the extracellular matrices of mammals. These materials can be prepared for use in mammals in tissue graft procedures.

In some aspects, the mammalian ECM is extracted from mammalian tissue/organs. For example, in some aspects, the mammalian ECM comprises the basement membrane (or transitional epithelial layer), tunica propria, tunica submucosa, tunica muscularis, tunica serosa, or a combination thereof from a mammalian tissue source. Thus, in some aspects, the mammalian ECM comprises the basement membrane (or transitional epithelial layer) from a mammalian tissue source. In some aspects, the mammalian ECM comprises the subjacent tunica propria from a mammalian tissue source. In some aspects, the mammalian ECM comprises the tunica submucosa from a mammalian tissue source. In some aspects, the mammalian ECM comprises the tunica muscularis from a mammalian tissue source. In some aspects, the mammalian ECM comprises the tunica serosa from a mammalian tissue source.

For example, small intestine submucosa (SIS) is described in U.S. Pat. No. 5,275,826; urinary bladder submucosa (UBS) is described in U.S. Pat. No. 5,554,389; stomach submucosa (SS) is described in U.S. Pat. No. 6,099,567; and liver submucosa (LS) or liver basement membrane (LBM) is described in U.S. Pat. No. 6,379,710, each of which is incorporated herein by reference for teachings of how to make and use these native extracellular matrices.

Thus, in some aspects, the mammalian ECM of the disclosed compositions and methods is small intestine submucosa (SIS). In some aspects, the mammalian ECM of the disclosed compositions and methods is urinary bladder submucosa (UBS). In some aspects, the mammalian ECM of the disclosed compositions and methods is stomach submucosa (SS). In some aspects, the mammalian ECM of the disclosed compositions and methods is liver submucosa (LS). In some aspects, the mammalian ECM of the disclosed compositions and methods is liver basement membrane (LBM).

In some aspects, the mammalian ECM of the disclosed compositions and methods is from dermis. For example, AlloDerm®, produced by LifeCell Corporation, is an acellular tissue matrix which is produced from normal human skin using processing techniques established to remove the epidermis and cells within the dermis without significantly altering the normal biochemistry and molecular architecture of the connective tissue matrix. The resulting product is in a freeze-dried form allowing extended shelf life and ease of shipping without degradation or loss of the normal tissue matrix components. AlloDerm® can retain decorin, hyaluronic acid, chondroitin sulfates, nidogen, growth factors and other biochemical proteins present in normal soft tissues. Additionally, AlloDerm® can contain the basement membranes of vascular channels and the orientation of elastin and collagen fibers of the starting dermal tissue.

In some aspects, the mammalian ECM of the disclosed compositions and methods is from fascia. In some aspects, the mammalian ECM of the disclosed compositions and methods is from parenchymal tissue. In some aspects, the mammalian ECM of the disclosed compositions and methods is from pericardium. In some aspects, the mammalian ECM of the disclosed compositions and methods is myocardial extracellular matrix. In some aspects, the mammalian ECM of the disclosed compositions and methods is from decellularized heart tissue, produced, for example, by coronary artery perfusion with detergents (Ott, et al., Nat Med. 2008 Feb.; 14(2): 213-21).

In some aspects, the mammalian ECM comprises a collagen scaffold derived from a mammalian tissue or organ source. The collagen scaffold from mammalian source can in some aspects comprise the basement membrane of the mammalian tissue source.

In some aspects, the mammalian ECM is produced in vitro. For example, the mammalian ECM can be produced from culture of mammalian cells. The mammalian ECM can be produced from proteins extracted from mammalian tissue/organs. For example, in some aspects, the mammalian ECM comprises an artificial collagen scaffold synthesized from collagen extracted from a mammalian tissue or organ source. Collagen from mammalian sources can be retrieved from matrix-containing tissues and used to form a matrix composition. Extracellular matrices can be synthesized from cell cultures as in the product manufactured by Matrigel™. In addition, dermal extracellular matrix material, subcutaneous extracellular matrix material, large intestine extracellular matrix material, placental extracellular matrix material, omentum extracellular matrix material, heart extracellular matrix material, and lung extracellular matrix material, can be used, derived and preserved similarly as described herein for the SIS, SS, LBM, and UBS materials. Other organ tissue sources of basement membrane for use in accordance with the disclosed compositions and methods include spleen, lymph nodes, salivary glands, prostate, pancreas and other secreting glands. In general, any tissue of a mammal that has an extracellular matrix can be used for developing an extracellular matrix component.

Collagenous matrix can be selected from a variety of commercially available collagen matrices or can be prepared from a wide variety of natural sources of collagen. Collagenous matrix for use in accordance with the disclosed compositions and methods can comprise highly conserved collagens, glycoproteins, proteoglycans, and glycosaminoglycans in their natural configuration and natural concentration. Collagens can be from animal sources, from plant sources, or from synthetic sources, all of which are available and standard in the art.

The proportion of scaffold material in the composition when native scaffold is used can be large, as the natural balance of extracellular matrix proteins in the native scaffolds usually represents greater than 90% of the extracellular matrix material by dry weight. Thus, the scaffold component of the composition by weight can be generally greater than 50% of the total dry weight of the composition. The scaffold can comprise an amount of the composition by weight greater than 60%, greater than 70%, greater than 80%, greater than 82%, greater than 84%, greater than 86%, greater than 88%, greater than 90%, greater than 92%, greater than 94%, greater than 96%, and greater than 98% of the total composition.

Native extracellular matrices can be prepared with care that their bioactivity for treating or preventing cardiac arrhythmia is preserved to the greatest extent possible. Key functions that can be preserved include control or initiation of cell adhesion, cell migration, cell differentiation, cell proliferation, cell death (apoptosis), stimulation of angiogenesis, proteolytic activity, enzymatic activity, cell motility, protein and cell modulation, activation of transcriptional events, provision for translation events, inhibition of some bioactivities, for example inhibition of coagulation, stem cell attraction, and chemotaxis. Assays for determining these activities are standard in the art. For example, material analysis can be used to identify the molecules present in the material composition. Also, in vitro cell adhesion tests can be conducted to make sure that the fabric or composition is capable of cell adhesion.

The disclosed compositions comprising mammalian ECM can be decellularized in order to render them non-immunogenic. In some aspects, the decellularization process is completed with some of the key protein functions retained, either by replacement of proteins incidentally extracted with the cells, or by adding exogenous cells to the matrix composition after cell extraction, which cells produce or carry proteins involved in treating or preventing cardiac arrhythmia.

When adding proteins to the extracellular matrix composition, the proteins can be simply added with the composition, or each protein can be covalently linked to a molecule in the matrix. Standard protein-molecule linking procedures can be used to accomplish the covalent attachment.

For decellularization when starting with a source tissue/organ as a source of mammalian ECM, source tissue/organ perfusion process can be used. The source tissue/organ can be perfused with a decellularization agent, for example 0.1% peracetic acid, rendering the organ acellular. The source tissue/organ can then be cut into portions and stored (e.g., in aqueous environment, liquid nitrogen, cold, freeze-dried, or vacuum-pressed) for later use. Any appropriate decellularizing agent can be used in source tissue/organ perfusion process.

With regard to submucosal tissue, extractions can be carried out near neutral pH (in a range from about pH 5.5 to about pH 7.5) in order to preserve the presence of growth factors in the matrices. Alternatively, acidic conditions (i.e., less than pH 5.5) can be used to preserve the presence of glycosaminoglycan components, at a temperature in a range between 0 and 50 degrees centigrade. In order to regulate the acidic or basic environment for these aqueous extractions, a buffer and chaotropic agent (generally at a concentration from about 2 M to about 8 M) can be selected, such as urea (at a concentration from about 2 M to 4 M), guanidine (at a concentration from about 2 M to about 6 M, most typically about 4 M), sodium chloride, magnesium chloride, and non-ionic or ionic surfactants. Urea at 2 M in pH 7.4 provides extraction of FGF-2 and the glycoprotein fibronectin. Using 4 M guanidine with pH 7.4 buffer yields a fraction having transforming growth factor beta. (TGF-$\beta$).

Because of the collagenous structure of basement membrane and the desire to minimize degradation of the membrane structure during cell dissociation, collagen specific enzyme activity can be minimized in the enzyme solutions used in the cell-dissociation step. For example, source tissue/organ can be treated with a calcium chelating agent or chaotropic agent such as a mild detergent such as Triton 100. The cell dissociation step can also be conducted using a calcium chelating agent or chaotropic agent in the absence of an enzymatic treatment of the tissue/organ. The cell-dissociation step can be carried out by suspending source tissue slices in an agitated solution containing about 0.05 to about 2%, more typically about 0.1 to about 1% by weight protease, optionally containing a chaotropic agent or a calcium chelating agent in an amount effective to optimize release and separation of cells from the basement membrane without substantial degradation of the membrane matrix.

After contacting the source tissue/organ with the cell-dissociation solution for a time sufficient to release all cells from the matrix, the resulting tissue/organ basement membrane can be rinsed one or more times with saline and optionally stored in a frozen hydrated state or a partially dehydrated state until used as described below. The cell-dissociation step can require several treatments with the cell-dissociation solution to release substantially all cells from the basement membrane. The source tissue/organ can be treated with a protease solution to remove the component cells, and the resulting extracellular matrix material is further treated to remove or inhibit any residual enzyme activity. For example, the resulting basement membrane can be heated or treated with one or more protease inhibitors.

Basement membrane or other native extracellular matrix scaffolds can be sterilized using conventional sterilization techniques including tanning with glutaraldehyde, formaldehyde tanning at acidic pH, ethylene oxide treatment, propylene oxide treatment, gas plasma sterilization, gamma radiation, and peracetic acid sterilization. A sterilization technique which does not significantly weaken the mechanical strength and biotropic properties of the material is preferably used. For example, it is believed that strong gamma radiation can cause loss of strength in the graft material. Example sterilization techniques include exposing the graft to peracetic acid, low dose gamma irradiation, gas plasma sterilization, and high-pressure/supercritical carbon dioxide.

ii. Synthetic ECM

Also disclosed are compositions comprising synthetic ECM for use in the disclosed methods. Synthetic ECM for use in the disclosed compositions and methods can be formed using synthetic molecules that polymerize much like native collagen and which form a scaffold environment that mimics the native environment of mammalian ECM scaffolds. According, such materials as polyethylene terephthalate fiber (Dacron®™), polytetrafluoroethylene (PTFE), glutaraldehyde-cross linked pericardium, polylactate (PLA), polyglycol (PGA), hyaluronic acid, polyethylene glycol (PEG), polyethylene, nitinol, and collagen from non-animal sources (such as plants or synthetic collagens), can be used as components of a synthetic extracellular matrix scaffold. The synthetic materials listed are standard in the art, and forming hydrogels and matrix-like materials with them is also standard. Their effectiveness can be tested in vivo as disclosed earlier, by testing in mammals, along with components that typically constitute native extracellular matrices, particularly the growth factors and cells responsive to them.

The extracellular matrix-like materials are described generally in Rosso et al. (Journal of Cellular Physiology 199:174-180, 2004), which is incorporated by reference herein for the teachings of how to make and use these materials. In addition, some extracellular matrix-like materials are listed here. Particularly useful biodegradable and/or bioabsorbable polymers include polylactides, polyglycolides, polycarprolactone, polydioxane and their random and block copolymers. Examples of specific polymers include poly D,L-lactide, polylactide-co-glycolide (85:15) and polylactide-co-glycolide (75:25). The biodegradable and/or bioabsorbable polymers used in the fibrous matrix of the disclosed compositions and methods can have a molecular weight in the range of about 1,000 to about 8,000,000 g/mole, including about 4,000 to about 250,000 g/mole. The biodegradable and/or bioabsorbable fiberizable material can be a biodegradable and bioabsorbable polymer. Examples of suitable polymers can be found in Bezwada, Rao S. et al. (1997) Poly(p-Dioxanone) and its copolymers, in Handbook of Biodegradable Polymers, A. J. Domb, J. Kost and D. M. Wiseman, editors, Hardwood Academic Publishers, The Netherlands, pp. 29-61. The biodegradable and/or bioabsorbable polymer can contain a monomer selected from the group consisting of a glycolide, lactide, dioxanone, caprolactone, trimethylene carbonate, ethylene glycol and lysine. The material can be a random copolymer, block copolymer or blend of monomers, homopolymers, copolymers, and/or heteropolymers that contain these monomers. The biodegradable and/or bioabsorbable polymers can contain bioabsorbable and biodegradable linear aliphatic polyesters such as polyglycolide (PGA) and its random copolymer poly(glycolide-co-lactide-) (PGA-co-PLA). The FDA has approved these polymers for use in surgical applications, including medical sutures. An advantage of these synthetic absorbable materials is their degradability by simple hydrolysis of the ester backbone in aqueous environments, such as body fluids. The degradation products are ultimately metabolized to carbon dioxide and water or can be excreted via the kidneys. These polymers are very different from cellulose-based materials, which cannot be absorbed by the body.

Other examples of suitable biocompatible polymers are polyhydroxyalkyl methacrylates including ethylmethacrylate, and hydrogels such as polyvinylpyrrolidone, polyacrylamides, etc. Other suitable bioaborbable materials are biopolymers which include collagen, gelatin, alginic acid, chitin, chitosan, fibrin, hyaluronic acid, dextran, polyamino acids, polylysine and copolymers of these materials. Any glycosaminoglycan (GAG) type polymer can be used. GAGs can include, e.g., heparin, chondroitin sulfate A or B, and hyaluronic acid, or their synthetic analogues. Any combination, copolymer, polymer or blend thereof of the above examples is contemplated for use according to the disclosed compositions and methods. Such bioabsorbable materials can be prepared by known methods.

Nucleic acids from any source can be used as a polymeric biomaterial. Sources include naturally occurring nucleic acids as well as synthesized nucleic acids. Nucleic acids suitable for use in the disclosed compositions and methods include naturally occurring forms of nucleic acids, such as DNA (including the A, B and Z structures), RNA (including mRNA, tRNA, and rRNA together or separated) and cDNA, as well as any synthetic or artificial forms of polynucleotides. The nucleic acids used in the disclosed compositions and methods can be modified in a variety of ways, including by cross linking, intra-chain modifications such as methylation and capping, and by copolymerization. Additionally, other beneficial molecules can be attached to the nucleic acid chains. The nucleic acids can have naturally occurring sequences or artificial sequences. The sequence of the nucleic acid can be irrelevant for many aspects of the disclosure. However, special sequences can be used to prevent any significant effects due to the information coding properties of nucleic acids, to elicit particular cellular responses or to govern the physical structure of the molecule. Nucleic acids can be used in a variety of crystalline structures both in finished biomaterials and during their production processes. Nucleic acid crystalline structure can be influenced by salts used with the nucleic acid. For example, Na, K, Bi, and Ca salts of DNA all have different precipitation rates and different crystalline structures. Additionally, pH influences crystalline structure of nucleic acids.

The physical properties of the nucleic acids can also be influenced by the presence of other physical characteristics. For example, inclusion of hairpin loops can result in more elastic biomaterials or can provide specific cleavage sites. The nucleic acid polymers and copolymers produced can be used for a variety of tissue engineering applications, including to increase tissue tensile strength, improve wound healing, speed up wound healing, as templates for tissue formation, to guide tissue formation, to stimulate nerve growth, to improve vascularization in tissues, as a biodegradable adhesive, as device or implant coating, or to improve the function of a tissue or body part. The polymers can also more specifically be used as sutures, scaffolds and wound dressings. The type of nucleic acid polymer or copolymer used can affect the resulting chemical and physical structure of the polymeric biomaterial.

iii. Combinations

The herein disclosed composition can comprise combinations of mammalian ECM from two or more sources or in two or more distinct forms. Thus, the disclosed compositions can comprise any combination of native and/or synthetic mammalian ECMs disclosed herein.

Thus, for example, the composition can comprise mammalian ECM combinations from such sources as, for example but not limited to, small intestine submucosa, liver basement membrane, stomach submucosa, urinary bladder submucosa, placental basement membrane, pancreatic basement membrane, large intestine submucosa, lung interstitial membrane, respiratory tract submucosa, heart extracellular matrix, dermal matrix, and in general extracellular matrix from any mammalian fetal tissue. Any one of these tissue sources can provide extracellular matrix that can then be manipulated into a designated form (liquid, semi-solid, or solid form), for use in a composition.

The combinations of mammalian ECM from two or more sources can be mixed solids, mixed liquids, mixed emulsions, mixed gels, mixed pastes, or mixed solid particulates. All of these compositions are mixtures of extracellular matrices from two or more sources, for example mixtures of powders or particulates from two or more extracellular matrices, mixtures of pastes from two or more extracellular matrices, mixtures of emulsions or gels from two or more extracellular matrices and mixtures of liquids from two or more extracellular matrices.

The compositions can be made from three mammalian tissue sources, four mammalian tissue sources, five mammalian tissue sources, six mammalian tissue sources, and conceivably up to ten or more tissue sources. These tissue sources can be from the same mammal (for example the same cow, the same pig, the same rodent, the same human, etc.), the same species of mammal (e.g. cow, pig, rodent, human), or different species of mammals (for example liver matrix from a pig, small intestine submucosa from a cow, and urinary bladder submucosa from a dog, all mixed together in the composition).

The compositions can comprise two or more liquid matrices (from different tissue sources) combined together. The composition can be two or more emulsion matrices (from different tissue sources) combined together. The composition can be two or more particulate matrices (from different tissue sources) combined together. The composition can be a liquid mixture of two or more extracellular matrices.

For example, a composition can comprise a combination of SIS in sheet, particulate, emulsion, gel or liquid form with SS, or LBM, or UBS in sheet, particulate, emulsion, gel or liquid form. For example, a composition can comprise a combination of SS in sheet, particulate, emulsion, gel or liquid form with SIS, or LBM, or UBS in sheet, particulate, emulsion, gel or liquid form. For example, a composition can comprise a combination of LBM in sheet, particulate, emulsion, gel or liquid form with SS, or SIS, or UBS in sheet, particulate, emulsion, gel or liquid form. For example, a composition can comprise a combination of UBS in sheet, particulate, emulsion, gel or liquid form with SS, or SIS, or LBM in sheet, particulate, emulsion, gel or liquid form.

The disclosed compositions can comprise combinations of mammalian ECM from one or more sources but in two or more distinct forms. For example, a composition can comprise a gel matrix combined with a particulate matrix. In some aspects, mammalian ECM in particulate form can be dusted onto mammalian ECM in a sheet form.

In some aspects, the composition can comprise a combination of SIS, SS, or LBM, or UBS in sheet, emulsion, gel or liquid form with SIS, SS, or LBM, or UBS in particulate form. In some aspects, the composition can comprise a combination of SIS, SS, or LBM, or UBS in particulate, emulsion, gel or liquid form with SIS, SS, or LBM, or UBS in sheet form. In some aspects, the composition can comprise a combination of SIS, SS, or LBM, or UBS in sheet, particulate, gel or liquid form with SIS, SS, or LBM, or UBS in emulsion form. In some aspects, the composition can comprise a combination of SIS, SS, or LBM, or UBS in sheet, particulate, emulsion, or liquid form with SIS, SS, or LBM, or UBS in gel form. In some aspects, the composition can comprise a combination of SIS, SS, or LBM, or UBS in sheet, particulate, emulsion, or gel form with SIS, SS, or LBM, or UBS in liquid form.

As disclosed herein, the composition comprising mammalian ECM can be prepared for preferred consistency. For example, mammalian ECM can be prepared as a combination of gel and particulate in a ratio optimal to prevent dissipation into the blood stream. For example, the composition comprising mammalian ECM can comprise about 40% ECM in gel form and about 60% ECM in dry particulate form. Thus, disclosed herein is a composition comprising mammalian ECM in both gel and dry particulate forms, wherein the gel form comprises about 10, 15, 20, 25, 30, 35, 36, 37, 38, 39, 40, 41, 42, 43, 44, 45, 50% of the ECM in the composition. Thus, the dry particulate form can comprise about 90, 85, 80, 75, 70, 65, 64, 63, 62, 61, 60, 59, 58, 57, 56, 55, 50% of the ECM in the composition.

Selection of the concentrations of the liquid or semi-solid compositions (liquids, gels, emulsions, or pastes) is important. For example, the liquid forms can be present in a range of concentrations, from very dilute at about 0.001 mg/ml to greater concentrations of up to about 200 mg/ml. The concentrations can further be found in more specific ranges such as, for example, the following set of ranges: from about 5 mg/ml to about 150 mg/ml, from about 10 mg/ml to about 125 mg/ml, from about 25 mg/ml to about 100 mg/ml, from about 20 mg/ml to about 75 mg/ml, from about 25 mg/ml to about 60 mg/ml, from about 30 mg/ml to about 50 mg/ml, from about 35 mg/ml to about 45 mg/ml, and from about 40 mg/ml to about 42 mg/ml. This set of ranges is exemplary and not intended to be exhaustive. It is contemplated that any value within any of these specifically listed ranges is a reasonable and useful value for a concentration of a liquid or semi-solid component of the composition.

The emulsion can be more concentrated than a liquid form and can retain a shape which can be useful in applying the matrix composition to certain parts of the body, hence its characterization as a "semi-solid". The emulsion can be concentrated enough to form shapes like a plug or other configuration suited to the site at which the matrix composition is being applied. Thick emulsion can be painted or otherwise applied at a site as a paste, and dusted with solid particulate on top of the emulsion. The solid particulate can be reconstituted to form the emulsion, or can be applied dry as a particulate powder which can dust a region in the subject being treated.

Dry particulate or reconstituted particulate that forms an emulsion of two or more mammalian ECM can be mixed together in some proportion. For example, 50% of SIS can be mixed with 50% of SS in a vial. This mixture can then be fluidized by hydrating it in a suitable buffer, for example saline. The hydration can be accomplished to a desired concentration of the mammalian ECM mixture, for example in a range from about 0.001 mg/ml to about 200 mg/ml. The concentrations can further be found in more specific ranges such as for example the following set of ranges: from about 5 mg/ml to about 150 mg/ml, from about 10 mg/ml to about 125 mg/ml, from about 25 mg/ml to about 100 mg/ml, from about 20 mg/ml to about 75 mg/ml, from about 25 mg/ml to about 60 mg/ml, from about 30 mg/ml to about 50 mg/ml, from about 35 mg/ml to about 45 mg/ml, and from about 40 mg/ml. to about 42 mg/ml. This set of ranges is exemplary and not intended to be exhaustive. It is contemplated that any value within any of these specifically listed ranges is a reasonable and useful value for a concentration of a liquid or semi-solid component of the composition.

The lower the concentration of extracellular matrix the more liquid the composition will be. The higher the concentration of extracellular matrix the more the composition approaches a gel-like emulsion or semi-solid consistency. The ratio of the mixtures of the two (or more) extracellular matrices in any given composition from different sources (or the same source) can be unequal. So for example, LBM can be present at 75% and SIS can be present at 25%, i.e., a 3:1 ratio). Any suitable ratio can be used: 1:1, 1:2, 1:3, 1:4, 1:5, and so on. Where 3 or more tissue sources of extracellular matrix are represented in the composition, the same type of balance or imbalance in the amounts of the matrices can occur. For example, for extracellular matrix from 3 sources, each source can be present in equal proportions, i.e., 1:1:1 (33%/33%/33%). Alternatively, a disproportionate amount of the particulate can be from one source, e.g., 2:1:1 (50%/25%/25%). Likewise, all three sources can be present in disproportionate amounts, e.g., 50%/30%/20%.

The two or more mammalian ECMs can be fluidized (or emulsified) separately and the fluidized or emulsified compositions mixed together. As another alternative, the two or more mammalian ECMs can be fluidized or emulsified separately and administered separately. In addition, the two or more mammalian ECMs can remain in particulate solid form and be mixed together in a vial for administration as a solid combination particulate. Rehydration of a dry particulate mammalian ECM mixture can be accomplished just prior to use.

2. Proteins

The disclosed compositions comprising mammalian ECM can further comprise exogenous proteins, such as those normally found in mammalian ECM. The protein can be a collagen, a proteoglycan, a glycosaminoglycan (GAG) chain, a glycoprotein, a growth factor, a cytokine, a cell-surface associated protein, a cell adhesion molecule (CAM), an angiogenic growth factor, an endothelial ligand, a matrikine, a matrix metalloprotease, a cadherin, an immunoglobulin, a fibril collagen, a non-fibrillar collagen, a basement membrane collagen, a multiplexin, a small-leucine rich proteoglycan, decorin, biglycan, a fibromodulin, keratocan, lumican, epiphycan, a heparan sulfate proteoglycan, perlecan, agrin, testican, syndecan, glypican, serglycin, selectin, a lectican, aggrecan, versican, nuerocan, brevican, cytoplasmic domain-44 (CD-44), macrophage stimulating factor, amyloid precursor protein, heparin, chondroitin sulfate B (dermatan sulfate), chondroitin sulfate A, heparan sulfate, hyaluronic acid, fibronectin (Fn), tenascin, elastin, fibrillin, laminin, nidogen/entactin, fibulin I, fibulin II, integrin, a transmembrane molecule, platelet derived growth factor (PDGF), epidermal growth factor (EGF), transforming growth factor alpha (TGF-alpha), transforming growth factor beta (TGF-β), fibroblast growth factor-2 (FGF-2) (also called basic fibroblast growth factor (bFGF)), thrombospondin, osteopontin, angiotensin converting enzyme (ACE), or a vascular epithelial growth factor (VEGF). This list is not intended to be exhaustive.

Thus, the herein disclosed compositions comprising a mammalian ECM can comprise collagen I and III, elastin, laminin, CD44, hyaluronan, syndecan, bFGF, HGF, PDGF, VEGF, Fn, tenascin, heparin, heparan sulfate, chondroitin sulfate B, integrins, decorin, TGF-β, or a combination thereof.

3. Cells

In some aspects, the herein disclosed compositions comprising mammalian ECM further comprise one or more cells. In some aspects the cells are non-native, i.e., heterologous to the mammalian ECM. In some aspects, the cells are stem cells. A non-exhaustive list of stem cells include human embryonic stem cell, a fetal cardiomyocyte, a myofibroblast, a mesenchymal stem cell, an autotransplanted expanded cardiomyocyte, an adipocyte, a totipotent cell, a pluripotent cell, a blood stem cell, a myoblast, an adult stem cell, a bone marrow cell, a mesenchymal cell, an embryonic stem cell, a parenchymal cell, an epithelial cell, an endothelial cell, a mesothelial cell, a fibroblast, an osteoblast, a chondrocyte, an exogenous cell, an endogenous cell, a stem cell, a hematopoietic stem cell, a pluripotent stem cell, a bone marrow-derived progenitor cell, a progenitor cell, a myocardial cell, a skeletal cell, a fetal cell, an embryonic cell, an undifferentiated cell, a multi-potent progenitor cell, a unipotent progenitor cell, a monocyte, a cardiomyocyte, a cardiac myoblast, a skeletal myoblast, a macrophage, a capillary endothelial cell, a xenogenic cell, an allogenic cell, an adult stem cell, and a post-natal stem cell.

In some aspects, the stem cells have the potential to differentiate into cardiac tissue cells. Thus, in some aspects, the stem cells are pluripotent. In some aspects, the stem cells are angioblasts or hemangioblasts. In some aspects, the stem cells are myoblasts. Stem cells can be derived and maintained using standard methods for stem cell culture.

4. Pharmaceuticals

The herein disclosed compositions comprising mammalian ECM can further comprise any known or newly discovered substance that can be administered to the heart of a subject. For example, the herein disclosed compositions comprising mammalian ECM can further comprise an antiarrhythmic agent. Antiarrhythmic agents are a group of pharmaceuticals that are used to suppress fast and/or irregular rhythms of the heart (cardiac arrhythmias).

The Vaughan Williams classification, introduced in 1970, is one of the most widely used classification schemes for antiarrhythmic agents. This scheme classifies a drug based on the primary mechanism of its antiarrhythmic effect. There are five main classes in the Vaughan Williams classification of antiarrhythmic agents: Class I agents interfere with the sodium (Na+) channel; Class II agents are anti-sympathetic nervous system agents (most agents in this class are beta blockers); Class III agents affect potassium (K+) efflux; Class IV agents affect calcium channels and the AV node; and Class V agents work by other or unknown mechanisms.

Class Ia agents include Quinidine, Procainamide, and Disopyramide. Class Ib agents include Lidocaine, Phenytoin, and Mexiletine. Class Ic agents include Flecainide, Propafenone, and Moricizine. Class II agents include Propranolol, Esmolol, Timolol, Metoprolol, and Atenolol. Class III agents include Amiodarone, Sotalol, Ibutilide, and Dofetilide. Class IV agents include Verapamil, and Diltiazem. Class V agents include Adenosine and Digoxin.

Thus, the herein disclosed compositions comprising mammalian ECM can further comprise one or more of Quinidine, Procainamide, Disopyramide, Lidocaine, Phenytoin, Mexiletine, Flecainide, Propafenone, Moricizine, Propranolol, Esmolol, Timolol, Metoprolol, Atenolol, Amiodarone, Sotalol, Ibutilide, Dofetilide, Verapamil, Diltiazem, Adenosine and Digoxin.

The provided compositions can further comprise one or more antibiotics (e.g., Aminoglycosides, Cephalosporins, Chloramphenicol, Clindamycin, Erythromycins, Fluoroquinolones, Macrolides, Azolides, Metronidazole, Penicillins, Tetracyclines, Trimethoprim-sulfamethoxazole, and Vancomycin).

The provided compositions can further comprise one or more steroids (e.g., Andranes (e.g., Testosterone), Cholestanes (e.g., Cholesterol), Cholic acids (e.g., Cholic acid), Corticosteroids (e.g., Dexamethasone), Estraenes (e.g., Estradiol), and Pregnanes (e.g., Progesterone).

The provided compositions can further comprise one or more classes of narcotic and non-narcotic analgesics, including, but not limited to, Morphine, Codeine, Heroin, Hydromorphone, Levorphanol, Meperidine, Methadone, Oxydone, Propoxyphene, Fentanyl, Methadone, Naloxone, Buprenorphine, Butorphanol, Nalbuphine, and Pentazocine.

The provided compositions can further comprise one or more anti-inflammatory agents, including, but not limited to, Alclofenac, Alclometasone Dipropionate, Algestone Acetonide, alpha Amylase, Amcinafal, Amcinafide, Amfenac Sodium, Amiprilose Hydrochloride, Anakinra, Anirolac, Anitrazafen, Apazone, Balsalazide Disodium, Bendazac, Benoxaprofen, Benzydamine Hydrochloride, Bromelains, Broperamole, Budesonide, Carprofen, Cicloprofen, Cintazone, Cliprofen, Clobetasol Propionate, Clobetasone Butyrate, Clopirac, Cloticasone Propionate, Cormethasone Acetate, Cortodoxone, Decanoate, Deflazacort, Delatestryl, Depo-Testosterone, Desonide, Desoximetasone, Dexamethasone Dipropionate, Diclofenac Potassium, Diclofenac Sodium, Diflorasone Diacetate, Diflumidone Sodium, Diflunisal, Difluprednate, Diftalone, Dimethyl Sulfoxide, Drocinonide, Endrysone, Enlimomab, Enolicam Sodium, Epirizole, Etodolac, Etofenamate, Felbinac, Fenamole, Fenbufen, Fenclofenac, Fenclorac, Fendosal, Fenpipalone, Fentiazac, Flazalone, Fluazacort, Flufenamic Acid, Flumizole, Flunisolide Acetate, Flunixin, Flunixin Meglumine, Fluocortin Butyl, Fluorometholone Acetate, Fluquazone, Flurbiprofen, Fluretofen, Fluticasone Propionate, Furaprofen, Furobufen, Halcinonide, Halobetasol Propionate, Halopredone Acetate, Ibufenac, Ibuprofen, Ibuprofen Aluminum, Ibuprofen Piconol, Ilonidap, Indomethacin, Indomethacin Sodium, Indoprofen, Indoxole, Intrazole, Isofluпредone Acetate, Isoxepac, Isoxicam, Ketoprofen, Lofemizole Hydrochloride, Lomoxicam, Loteprednol Etabonate, Meclofenamate Sodium, Meclofenamic Acid, Meclorisone Dibutyrate, Mefenamic Acid, Mesalamine, Meseclazone, Mesterolone, Methandrostenolone, Methenolone, Methenolone Acetate, Methylprednisolone Suleptanate, Momiflumate, Nabumetone, Nandrolone, Naproxen, Naproxen Sodium, Naproxol, Nimazone, Olsalazine Sodium, Orgotein, Orpanoxin, Oxandrolane, Oxaprozin, Oxyphenbutazone, Oxymetholone, Paranyline Hydrochloride, Pentosan Polysulfate Sodium, Phenbutazone Sodium Glycerate, Pirfenidone, Piroxicam, Piroxicam Cinnamate, Piroxicam Olamine, Pirprofen, Prednazate, Prifelone, Prodolic Acid, Proquazone, Proxazole, Proxazole Citrate, Rimexolone, Romazarit, Salcolex, Salnacedin, Salsalate, Sanguinarium Chloride, Seclazone, Sermetacin, Stanozolol, Sudoxicam, Sulindac, Suprofen, Talmetacin, Talniflumate, Talosalate, Tebufelone, Tenidap, Tenidap Sodium, Tenoxicam, Tesicam, Tesimide, Testosterone, Testosterone Blends, Tetrydamine, Tiopinac, Tixocortol Pivalate, Tolmetin, Tolmetin Sodium, Triclonide, Triflumidate, Zidometacin, and Zomepirac Sodium.

The provided compositions can further comprise one or more lipid-lowering drugs. As used herein, the term "lipid-lowering drug" refers to a drug that can be administered to a subject to reduce the serum levels of various heart disease-associated lipids, including, but not limited to, cholesterol, low-density lipoprotein (LDL), very low-density lipoprotein (VLDL), and triglycerides.

For example, the lipid-lowering drugs can be statins, including, but not limited to, Lovastatin, Simvastatin, Atorvastatin, Fluvastatin, Pravastatin, Rosuvastatin, Cervistatin, and Pitavastatin. It is contemplated that any statin drug, now known or developed in the future, having lipid-reducing and/or anti-inflammatory properties can be used in the compositions described herein.

The provided compositions can further comprise one or more anti-histaminic agents, including, but not limited to, Ethanolamines (like diphenhydramine carbinoxamine), Ethylenediamine (like tripelennamine pyrilamine), Alkylamine (like chlorpheniramine, dexchlorpheniramine, brompheniramine, triprolidine), astemizole, loratadine, fexofenadine, Bropheniramine, Clemastine, Acetaminophen, Pseudoephedrine, and Triprolidine.

The provided compositions can further comprise one or more antineoplastic drugs, including, but not limited to, Acivicin, Aclarubicin, Acodazole Hydrochloride, AcrQnine, Adozelesin, Aldesleukin, Altretamine, Ambomycin, Ametantrone Acetate, Aminoglutethimide, Amsacrine, Anastrozole, Anthramycin, Asparaginase, Asperlin, Azacitidine, Azetepa, Azotomycin, Batimastat, Benzodepa, Bicalutamide, Bisantrene Hydrochloride, Bisnafide Dimesylate, Bizelesin, Bleomycin Sulfate, Brequinar Sodium, Bropirimine, Busulfan, Cactinomycin, Calusterone, Caracemide, Carbetimer, Carboplatin, Carmustine, Carubicin Hydrochloride, Carzelesin, Cedefingol, Chlorambucil, Cirolemycin, Cisplatin, Cladribine, Crisnatol Mesylate, Cyclophosphamide, Cytarabine, Dacarbazine, Dactinomycin, Daunorubicin Hydrochloride, Decitabine, Dexonnaplatin, Dezaguanine, Dezaguanine Mesylate, Diaziquone, Docetaxel, Doxorubicin, Doxorubicin Hydrochloride, Droloxifene, Droloxifene Citrate, Dromostanolone Propionate, Duazomycin, Edatrexate, Eflomithine Hydrochloride, Elsamitrucin, Enloplatin, Enpromate, Epipropidine, Epirubicin Hydrochloride, Erbulozole, Esorubicin Hydrochloride, Estramustine, Estramustine Phosphate Sodium, Etanidazole, Ethiodized Oil I 131, Etoposide, Etoposide Phosphate, Etoprine, Fadrozole Hydrochloride, Fazarabine, Fenretinide, Floxuridine, Fludarabine Phosphate, Fluorouracil, Flurocitabine, Fosquidone, Fostriecin Sodium, Gemcitabine, Gemcitabine Hydrochloride, Gold Au 198, Hydroxyurea, Idarubicin Hydrochloride, Ifosfamide, Ilmofosine, Interferon Alfa-2a, Interferon Alfa-2b, Interferon Alfa-n1, Interferon Alfa-n3, Interferon Beta-Ia, Interferon Gamma-Ib, Iproplatin, Irinotecan Hydrochloride, Lanreotide Acetate, Letrozole, Leuprolide Acetate, Liarozole Hydrochloride, Lometrexol Sodium, Lomustine, Losoxantrone Hydrochloride, Masoprocol, Maytansine, Mechlorethamine Hydrochloride, Megestrol Acetate, Melengestrol Acetate, Melphalan, Menogaril, Mercaptopurine, Methotrexate, Methotrexate Sodium, Metoprine, Meturedepa, Mitindomide, Mitocarcin, Mitocromin, Mitogillin, Mitomalcin, Mitomycin, Mitosper, Mitotane, Mitoxantrone Hydrochloride, Mycophenolic Acid, Nocodazole, Nogalamycin, Onnaplatin, Oxisuran, Paclitaxel, Pegaspargase, Peliomycin, Pentamustine, Peplomycin Sulfate, Perfosfamide, Pipobroman, Piposulfan, Piroxantrone Hydrochloride, Plicamycin, Plomestane, Porfimer Sodium, Porfiromycin, Prednimustine, Procarbazine Hydrochloride, Puromycin, Puromycin Hydrochloride, Pyrazofurin, Riboprine, Rogletimide, Safingol, Safingol Hydrochloride, Semustine, Simtrazene, Sparfosate Sodium, Sparsomycin, Spirogennanium Hydrochloride, Spiromustine, Spiroplatin, Streptonigrin, Streptozocin, Strontium Chloride Sr 89, Sulofenur, Talisomycin, Taxane, Taxoid, Tecogalan Sodium, Tegafur, Teloxantrone Hydrochloride, Temoporfin, Teniposide, Teroxirone, Testolactone, Thiamiprine, Thioguanine, Thiotepa, Tiazofurin, Tirapazamine, Topotecan Hydrochloride, Toremifene Citrate, Trestolone Acetate, Triciribine Phosphate, Trimetrexate, Trimetrexate Glucuronate, Triptorelin, Tubulozole Hydrochloride, Uracil Mustard, Uredepa, Vapreotide, Verteporfin, Vinblastine Sulfate, Vincristine Sulfate, Vindesine, Vindesine Sulfate, Vinepidine Sulfate, Vinglycinate Sulfate, Vinleurosine Sulfate, Vinorelbine Tartrate, Vinrosidine Sulfate, Vinzolidine Sulfate, Vorozole, Zeniplatin, Zinostatin, and Zorubicin Hydrochloride.

The herein provide composition can further comprise one or more radiosensitizers, including, but not limited to, gemcitabine, 5-fluorouracil, pentoxifylline, and vinorelbine.

5. Carriers

The disclosed mammalian ECM can be combined, conjugated or coupled with or to carriers and other compositions to aid administration, delivery or other aspects of the ECM and their use. For convenience, such compositions are referred to herein as carriers. Carriers can, for example, be a small molecule, pharmaceutical drug, fatty acid, detectable marker, conjugating tag, nanoparticle, or enzyme.

The disclosed compositions can be used therapeutically in combination with a pharmaceutically acceptable carrier. By "pharmaceutically acceptable" is meant a material that is not biologically or otherwise undesirable, i.e., the material can be administered to a subject, along with the composition, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

Suitable carriers and their formulations are described in Remington: The Science and Practice of Pharmacy (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the composition, which matrices are in the form of shaped articles, e.g., films, liposomes or microparticles. It will be apparent to those persons skilled in the art that certain carriers may be more preferable depending upon, for example, the route of administration and concentration of composition being administered.

Pharmaceutical carriers are known to those skilled in the art. These most typically would be standard carriers for administration of drugs to humans, including solutions such as sterile water, saline, and buffered solutions at physiological pH.

Pharmaceutical compositions can include carriers, thickeners, diluents, buffers, preservatives, surface active agents and the like in addition to the molecule of choice. Pharmaceutical compositions can also include one or more active ingredients such as antimicrobial agents, anti-inflammatory agents, anesthetics, and the like.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, antioxidants, chelating agents, and inert gases and the like.

Formulations for topical administration can include ointments, lotions, creams, gels, drops, suppositories, sprays, liquids and powders. Conventional pharmaceutical carriers, aqueous, powder or oily bases, thickeners and the like can be necessary or desirable.

Compositions for oral administration include powders or granules, suspensions or solutions in water or non-aqueous media, capsules, sachets, or tablets. Thickeners, flavorings, diluents, emulsifiers, dispersing aids or binders can be desirable.

Some of the compositions can potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

D. METHODS OF MAKING THE COMPOSITIONS

The compositions disclosed herein and the compositions necessary to perform the disclosed methods can be made using any method known to those of skill in the art for that particular reagent or compound unless otherwise specifically noted. For example, U.S. Pat. No. 5,275,826, U.S. Pat. No. 5,554,389, U.S. Pat. No. 6,099,567, and U.S. Pat. No. 6,379,710, are disclosed herein by reference for methods of making compositions comprising small intestine submucosa (SIS), urinary bladder submucosa (UBS), stomach submucosa (SS), and liver submucosa (LS) or liver basement membrane (LBM), respectively.

E. EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in .degree. C. or is at ambient temperature, and pressure is at or near atmospheric.

1. Example 1

Retrospective Evaluation of New Onset Postoperative Atrial Fibrillation in Patients Receiving the CorMatrix® ECM®

A retrospective, multi-center, two-arm, chart review was conducted in which the CorMatrix®™ ECM™ was utilized. The objective of this retrospective trial was to assess whether utilization of the CorMatrix® ECM® to reconstruct the normal pericardial barrier can result in a lower rate of new onset postoperative atrial fibrillation as compared to patients who did not undergo pericardial closure.

CorMatrix® ECM® can be used for the reconstruction and repair of the pericardium following open heart surgery. Intact, the pericardium provides passive restraint to the heart preventing over dilation and helping to modulate abrupt volumetric changes. By reconstructing the pericardium with the CorMatrix® ECM®, the natural pericardial restraint can be restored. The purpose of this retrospective clinical trial was to assess if there is a reduction observed in new onset postoperative atrial fibrillation by analyzing patients who had their native pericardium reconstructed with the CorMatrix® ECM® as compared to those who did not undergo pericardial closure following isolated coronary artery bypass graft (CABG) procedures.

The CorMatrix® ECM® was supplied in four-ply sheets of various dimensions, which can be cut to size as the physician deems necessary for the procedure.

The definition of new onset postoperative atrial fibrillation used for this retrospective study is based on the definition used in the Society of Thoracic Surgeons (STS) Adult Cardiac Surgery Database 2007. The definition is as follows: "Indicate whether the patient had a new onset of Atrial Fibrillation/Flutter (AF) requiring treatment. Does not include recurrence of AF which had been present preoperatively. Do not include patients that had preoperative atrial fibrillation (treated or non-treated). The event must be of new origin.

All patients were required to meet the following inclusion criteria in order to be included as part of this retrospective clinical trial: this cardiac operation was the subject's first or primary cardiac operation, and the subject must have undergone an isolated CABG procedure.

Patients were not included as part of this retrospective clinical trial if one or more of the following exclusion criteria is met: prior history of atrial fibrillation, prior history of open heart surgery, prior history of pericarditis, prior history of amiodarone in the past six months, and concomitant valve surgery planned.

Patients who had their native pericardium reconstructed with the CorMatrix® ECM® had a statistically significant decrease in the incidence of A-fib as compared to those who did not undergo pericardial closure following isolated CABG procedures. The usual incidence of A-fib is around 25%. For these studies, the A-fib incidence was between 4% and 8% ($1/25$ and $4/52$).

2. Example 2

Modulation of Cardiac Remodeling with Acellular Matrix Emulsion is Associated with Myofibroblast Proliferation and Angiogenesis Via Recruiting C-Kit Positive Cells after Myocardial Infarction Degradation of native extracellular matrix (ECM) has been associated with maladaptive cardiac remodeling after infarction. As shown herein, xenogeneic acellular matrix emulsion injected into infarcted myocardium promoted myofibroblast proliferation and angiogenesis by recruiting host c-kit positive cells.

Sixty-four rats were subjected to 45 minutes regional ischemia followed by 3, 7, 21 and 42 days of reperfusion. Histological examination was performed by immunohistological staining, and cardiac function was analyzed using echocardiography. ECM emulsion (30-50 .mu.l) was injected into the area at risk myocardium after reperfusion and localization of the emulsion was continued with Masson Trichome staining. At 7 days of reperfusion, the population of c-kit positive cells within the emulsion area increased significantly relative to the control (32.+-0.6* vs. 15.+-0.3/1000 nuclei), consistent with significantly enhanced expression of 31 kDa stem cell factor detected by Western blotting. Along with this change, myofibroblasts accumulated in the emulsion region to a significant extent compared to the control (59.+-0.8* vs. 30.+-0.3/HPF). Strong immunoreactivity of VEGF was observed in the emulsion area and angiogenesis was significantly enhanced relative to the control, evidenced by increased density of .alpha.-smooth muscle actin-positive vessels (70.+-0.10* vs. 20.+-0.4/HPF) and vWF-positive vessels (95.+-0.14* vs. 34.+-0.8/HPF), respectively. At 42 days of reperfusion, echocardiography showed improvements in end-systolic volume (0.3.+-.0.1* vs. 0.6.+-.0.3 ml)), fractional shortening (33.+-0.5* vs. 24.+-0.6%) and ejection fraction (67.+-0.6* vs. 53.+-0.10%) in the emulsion group. The wall thickness of the infarcted middle anterior septum in the emulsion group was also significantly greater than that in the Control (0.19.+-.0.02* vs. 0.15.+-.0.02 cm).

Intramyocardial injection of an acellular extracellular matrix emulsion into the ischemic/reperfused myocardium attenuated maladaptive cardiac remodeling and preserved cardiac function, potentially mediated by enhanced myofibroblast proliferation and angiogenesis via recruiting c-kit positive cells. *p<0.05 emulsion vs. control.

What is claimed is:

1. A method of treating post-operative atrial fibrillation in a subject, comprising:
   providing an extracellular matrix (ECM) composition comprising acellular ECM from a mammalian tissue source, said ECM composition further comprising a statin and a Class II anti-arrhythmic agent selected from the group consisting of (RS)-1-(1-methylethylamino)-3-(1-naphthyloxy)propan-2-ol (Propranolol™), methyl (RS)-3-{4-[2-hydroxy-3-(propan-2-ylamino)propoxy]phenyl}propanoate (Esmolol™), (S)-1-(tert-butylamino)-3-[(4-morpholin-4-yl-1,2,5-thiadiazol-3-yl)oxy]propan-2-ol (Timolol™), (RS)-1-(Isopropylamino)-3-[4-(2-methoxyethyl)phenoxy]propan-2-ol (Metoprolol™) and (RS)-2-{4-[2-Hydroxy-3-(propan-2-ylamino)propoxy]phenyl}acetamide (Atenolol™), said statin and Class II anti-arrhythmic agent being linked to said ECM, wherein, when said ECM composition is administered to damaged myocardium tissue of said subject, said statin interacts with said ECM and modulates inflammation of said myocardium tissue and induces myofibroblast proliferation and angiogenesis, and said Class II anti-arrhythmic agent modulates the sympathic nervous system of said subject, whereby said ECM composition modulates electrical activity in the heart of said subject; and
   delivering a therapeutically effective amount of said ECM composition directly to post-operative damaged myocardium tissue of said subject, wherein, said ECM composition modulates inflammation of said post-operative damaged myocardium tissue and induces said myofibroblast proliferation and angiogenesis and, thereby, bioremodeling and regeneration of new myocardium tissue and said Class II anti-arrhythmic agent modulates said sympathic nervous system, whereby said ECM composition reduces incidence of post-operative atrial fibrillation of said subject.

2. The method of claim 1, wherein said acellular ECM is selected from the group consisting of small intestinal submucosa, urinary bladder submucosa, stomach submucosa, and liver basement membrane.

3. The method of claim 1, wherein said statin is selected from the group consisting of lovastatin, simvastatin, atorvastatin, fluvastatin, pravastatin, rosuvastatin, cerivastatin and pitavastatin.

* * * * *